(12) United States Patent
Cox et al.

(10) Patent No.: US 7,179,803 B1
(45) Date of Patent: Feb. 20, 2007

(54) METHOD OF MODULATING ION CHANNEL FUNCTIONAL ACTIVITY

(75) Inventors: Graeme Cox, Bawley Point (AU); Gary Ewart, Hackett (AU); Peter Gage, Queanbetan (AU)

(73) Assignee: Australian National University, Australian Capital Territory (AU)

( * ) Notice: Subject to any disclaimer, the term of this patent is extended or adjusted under 35 U.S.C. 154(b) by 0 days.

(21) Appl. No.: 09/807,277

(22) PCT Filed: Oct. 12, 1999

(86) PCT No.: PCT/AU99/00872

§ 371 (c)(1),
(2), (4) Date: Mar. 1, 2002

(87) PCT Pub. No.: WO00/21538

PCT Pub. Date: Apr. 20, 2000

(30) Foreign Application Priority Data

Oct. 12, 1998 (AU) .................................... PP6464

(51) Int. Cl.
*A61K 31/55* (2006.01)
*A61K 31/497* (2006.01)
*A61K 31/4965* (2006.01)

(52) U.S. Cl. .................. 514/217.05; 514/252.1; 514/255.06

(58) Field of Classification Search ............ 514/252.1, 514/217.05, 255.06
See application file for complete search history.

(56) References Cited

U.S. PATENT DOCUMENTS

| | | | | |
|---|---|---|---|---|
| 4,085,211 A | * | 4/1978 | Crago et al. | 514/252.11 |
| 5,215,991 A | * | 6/1993 | Burke | 514/249 |
| 5,506,231 A | * | 4/1996 | Lipton | 514/289 |

FOREIGN PATENT DOCUMENTS

| | | |
|---|---|---|
| JP | 07025768 | 1/1995 |
| WO | WO 90/09792 | 9/1990 |
| WO | WO 95/27510 | 10/1995 |
| WO | WO 95/27510 A | 10/1995 |

OTHER PUBLICATIONS

Balliet, J. W., et al., "Distinct Effects in Primary Macrophages and Lymphocytes of the Human Immunodeficiency virus Type 1 Accessory Gense *vpr*, *vpu*, and *nef*: Mutational analysis of a primary HIV-1 Isolate", *Virology*, 200:623-631 (1994).

(Continued)

*Primary Examiner*—Shengjun Wang
(74) *Attorney, Agent, or Firm*—Buchanan Ingersoll & Rooney PC

(57) ABSTRACT

The present invention relates generally to a method of retarding, reducing or otherwise inhibiting viral functional activity and, more particularly, to a method of reducing, retarding or otherwise inhibiting viral functional activity by down-regulating Vpu ion channel functional activity. Even more particularly, the present invention provides a method of treating HIV infection or AIDS by inhibiting Vpu ion channel mediated HIV replication.

17 Claims, 10 Drawing Sheets

OTHER PUBLICATIONS

Barry, M., et al., "Antiretroviral therapy for patients with HIV Disease", *Br J. Clin. Pharmacol.*, 45:221-228 (1998).

Benos, D.J., et al., "Envelope glycoprotein gp 120 of human immunodeficiency virus type 1 alters ion transport in astrocytes: Implications for AIDS dementia complex" *Proc. Natl. Acad. Sci. USA*, 91:494-498 (1994).

Bour, S., et al., The Human Immunodeficiency Virus Type 1 Vpu Protein Specifically Binds to the Cytoplasmc Domain of CD4: Implications for the Mechanism of Degradation, *J. Virol*, 69(3):1510-1520 (1995).

Bubien, J.K., et al. "HIV—gp 120 activates large—conductance apamin sensitive potassium channels in rat astrocytes" *Am. J. Physiol.*, 286(6, part 1): C1440-C1449 (1995).

Cragoe, E.J., et al., "Pryazine Diuretics. N-Amidino-3-amino-5-substituted 6-Halopyrazinecarbozmides", *J. Med. Chem.*, 10:66-75(1967).

Deeks, S.G., "Practical Issues Regarding the Use of Antiretroval Therapy for HIV Infection", *West J. Med.*, 168:133-139 (1998).

Duff, K.C., et al, "The Transmembrane Domain of Influenza A M2 Protein Forms Amantadine-Sensitive Proton Channels in Planar Lipid Bilayers", *Virology*, 190:485-489 (1992).

Ewart, G.D., et al., The Vpu Protein of Human Immunodeficiency Virus Type 1 Form Cation-Selective Ion Channels:, *J. Virol.*, 70(10):7108-7115 (1996).

Fear, W.R. et al., "Differential Tropism and Chemokine Receptor Expression of Human Immunodeficiency Virus Type 1 in Neonatal Monocytes, Monocyte-Derived Macrophages, and Placental Macrophages", *J. Virol.*, 72(2):1334-1344 (1998).

Friborg, J., et al., "Functional Analysis of the Phosphorylation Sites on the Human Immunodeficiency Virus Type 1 Vpu Protein", *J. Acquir. Immun Defic. Syndr. Hum. Retrovirol.*, 8:10-22 (1995).

Grice, et al., "Ion channels formed by HIV-1 Vpu: a modelling and simulation study", *FEBS Lett*, 405(3):299-304 (1997).

Hay,A.J., et al., "The molecular basis of the specific anti-influenza action of action of amantandine" *EMBO*, 4(11):3021-3024 (1985).

Jabbar, M.A., The Human Immunodeficiency Virus Type 1 Vpu Protein: Roles in Virus Release and CD4 Downregulation, Cleveland Clinic Foundation, Dept. of Molecular Biology, pp. 107-118.

Kelly, M.D., et al., "Cutting Edge: Dichotomous Effects of B-Chemokines on HIV Replication in Monoctyes and Monocyte-Derived Macrophages", *J. Immunol.*, 160:3091-3095 (1998).

Kleyman, T.R., et al, "Amiloride and its Analogs as Tools in Study of Ion Transport", *J. Membrane Biol.* 105:1-21(1988).

Klimkait, T., et al., "The Human Immunodeficiency viru Type 1-Specific Protein *vpu* Is Required for Efficient Virus Maturation and Release" *J. of Virology* 64(2):621-629 (1990).

Love, C.A., et al., "Stable high-copy-number bacteriophage λ promoter vectors for overproduction of proteins in*Escherichia coli"*, *Gene*, 176:49-53 (1996).

Lu, Y.A., et al., "Chemically unambiguous peptide immunogen: preparation, orientation and antigenicity of purified peptide conjugated to the multiple antigen peptide system", *Mol. Immun.*, 28(6):623-630 (1991).

Makutonina, A., et al., "Human Immunodeficiency virus infection of T-Lymphoblastoid Cells Reduces Intracellular pH" *J. Virol.*, 70(10):7049-7055 (1996).

Maldarelli, F., et al., "Human Immunodeficiency Virus Type 1 Vpu Protein Is an Oligomeric Type I Intgral Membrane Protein" *Jr. of Virology* 67(8):5056-5061(1993).

Miles, S.A., "Long-Term Therapeutic Stratgies in HIV", *J. Acquir. Immune Defic. Syndr. Hum. Retrovirol.*, 16(Suppl 1): S36-S41(1997).

Miles, S.A., "Introduction", *J. Acquir. Immune Defic. Syndr. Hum. Retrovirol.*16 Suppl 1: S1-2 (1997).

Miller, R.H., et al., "HIV accessory proteins as therapeutic targets", *Nat. Med.*, 3(4):389-394 (1997).

Mitsuya, H., "Development of Inhibitors of Reverse Transcriptase and Protease as Therapeutics Against HIV Infection", *Enzyme Inhibition*, 6:1-8 (1992).

Moore, J.P., et al., "Simulation of the HIV-1 VPU transmembrane domain as a pentameric bundle", *FEBS Lett*, 431(2):143-148 (1998).

Moore, J.P., "Coreceptors: Implications for HIV Pathogensis and Therapy", *Science*, 276:51-52 (1997).

Moyke, G.J., et al., "Antiretroviral therapy of HIV Infection", *Drugs*, 55(3):383-404 (1998).

Perezella, M.A., et al., "Trimethoprim-sulfamethoxazole hyperkalemia is an important complication regardless of dose" *Clinical Nephrology*, 46(3):187-192 (1996).

Piller, S.C., et al., "Vpr protein of human immunodeficiency virus type 1 forms cation-selective channels in planar lipid bilayers", *Proc. Natl. Acad. Sci*, 93:111-115 (1996).

Pinto,L.H., et al., "Influenza Virus $M_2$ Protein Has Ion Channel Activity", *Cell* 69:517-528 (1992).

Rachlis, A.R., et al., "Guidelines for antiretroviral therapy for HIV infection", *Cmaj*, 158:496-505 (1998).

Rosen, B.P., ATP-coupled Solute Transport Systems. *Escherichia coli and Salmonella typimurium*: Cellular and Molecular Biology 1: editor: Neidart, American Society for Microbiology 760-767 (1987).

Sansom, M.S.P., et al., "Influenza virus $M_2$ protein: a molecular modelling study of the ion channel", *Protein Engineering* 6(1):65-74 (1993).

Schlanger, L.E., et al., "K+-sparing diuretic actions of trimethoprim: Inhibition of Na+channels in distal nephron cells", *Kidney International*, 45:1070-1076 (1994).

Schubert, U. et al., "The Two Biological Activities of Human Immunodeficiency Virus Type 1 Vpu Protein Involve Two Separable Structural Domains", *J. Virol.*, 70(2):809-819 (1996a).

Schubert, U., et al., "The Human Immunodeficiency Virus Type I Encoded Vpu Protein is Phosophorylated by Casein Kinase-2 (CK-2) at Positions Ser52 and Ser56 within a Predicted α-Helix-Turnα-α-Helix-Motif", *J. Mol. Biol.*, 236:16-25 (1994).

Schubert, U., et al., "Human-immunodeficiency-virus-type-1-encoded Vpu is phosphorylated by casein Kinase II", *Eur. J. Biochem.*, 204:875-882 (1992).

Schubert, U., et al., "Identification of an ion channel activity of the Vpu transmembrane domain and its involvement in the regulation of virus release from HIV-1-infected cells", *FEBS Letters* 398:12-18 (1996).

Strebel, K., et al., "A Novel Gene of HIV-1, *vpu*, and Its 16-Kilodalton Product", *Science* 241:121-1223 (1988).

Sugrue, R.J., "Structural Characteristics of M3 Protein of Influenza A Viruses: Evidence That It Forms a Tetrametric Channel", *Virology* 180:617-624 (1991).

Thomas, M., et al., "HIV Integrase: a target for AIDS therapeutics", *Trends Biotechnol.*, 15:167-172 (1997).

Tosteson, M.T., et al., "Reconstruction of the Influenza Virus $M_2$ Ion Channel in Lipid Bilayers", *J. Membrane Biol.* 142:117-126 (1994).

Trono, D., "HIV Accessory Proteins: Leading Roles for the Supporting Cast", *Cell*, 82:189-192 (1995).

Varadhachary, A., et al., "A rapid method for reconstitution of bacterial membrane proteins", *Mol. Microbiol.*, 4(8):1407-1411 (1990).

Vella, S., et al., "Recent advances in antiretroviral therapy of HIV infection", *J. Biol. Regul. Homeost. Agents*, 11(1/2):60-63 (1997).

Volberding, P.A., et al., "Antiretroviral Therapy for HIV Infection", *Jama*, 279(17):1343-1344 (1998).

Volberding , P.A., et al., "An Aggressive Approach to HIV Antiretroviral Therapy", *Hosp Pract.* (Off Ed), 33:81-84, 87-90, 95-96 passim (1998).

Wang, C., et al., "Direct Measurement of the Influenza A virus $M_2$ Protein Ion channel Activity in Mammalian Cells", *Virology* 205:133-140 (1994).

Westervelt, p., et al:, "Dual Regulation of Silent and Productive Infection in Monocytes by Distinct Human Immunodeficiency Virus Type 1 Determinants", *J. Virol.*, 66(6):3925-3931 (1992).

Willbold, et al., "Secondary structure and tertiary fold of the human immunodeficiency virus protein U (Vpu) cytoplasmic domain insolution", *Eur. J. Biochem.*, 245(3): 581-588 (1997).

Willey, R.L., et al., "Human Immunodeficicency Virus Type 1 Vpu Protein Induces Rapid Degradation of CD4", *J. of Virology*, 66(12):7193-7200 (1992).

Wray, et al., "Solution Structure and Orientation of the Transmembrane Anchor Domain of the HIV-1-Encoded Virus Protein U by High-Resolution and Solid-State NMR Spectroscopy", *Biochemistry*, 38(16):5272-5282 (1999).

Yamato, I., et al., "Site-specific alteration of Argine 376, the Unique Positively Charged Amino Acid Residue in the Mid-membrane-spanning Regions of the Proline Carrier of *Escherichia Coli.* ", *J. of Biol. Chem.*, 269(8):5729-5724 (1994).

Supplemental European Search Report dated Sep. 15, 2004.

* cited by examiner

```
          10         20          30           40           50            60             70            80
           *          *           *            *            *             *              *             *
                                 -++         -+ ++        -+  -+          -                -  ++        - -
                                  ++         +             +   -          -                -  +         - -
MQPIPIVAIVALVVAILIAIVWSIVIIEYRKILRQRKIDRLIDRLIERAEDSGNESEGEISALVEMGVEMGHHAPWDVDDL
 *
```

Figure 1a

37°C, Pro⁻ plate

30°C, Pro⁻ plate

37°C, Met⁻ plate

METHOD OF MODULATING ION CHANNEL FUNCTIONAL ACTIVITY

FIELD OF THE INVENTION

The present invention relates generally to a method of retarding, reducing or otherwise inhibiting viral functional activity and, more particularly, to a method of reducing, retarding or otherwise inhibiting viral functional activity by down-regulating Vpu ion channel functional activity. Even more particularly, the present invention provides a method of treating HIV infection or AIDS by inhibiting Vpu ion channel mediated HIV replication.

BACKGROUND OF THE INVENTION

Bibliographic details of the publications alphabetically referred to in this specification are collected at the end of the description.

Currently, no single treatment method is completely effective against HIV infections. Combination therapies, using drugs that target a number of different aspects of HIV replication, have proven to be the most effective way of ameliorating AIDS symptoms and prolonging life expectancy (Barry et al, 1998; Deeks, 1998; Miles, 1997; Miles, 1998; Moyle et al, 1998; Rachlis and Zarowny, 1998; Vell et al, 1997; Volberding and Deeks, 1998; and Volberdin, 1998). For example, a measure of success has been achieved with drugs targeting the viral reverse transcriptase and protease enzymes (Miller and Sarver, 1997; Mitsuya, 1992; Moore, 1997; and Thomas and Brady, 1997).

The protein Vpu forms an ion channel encoded by HIV and has a number of known roles in the virus life cycle including down-regulation of cell surface expression of the CD4 virus receptor molecule, control of the exit of gp160 from the endoplasmic reticulum and its delivery to the cell surface and regulation of virion budding from the cell surface membrane. In the absence of Vpu, HIV replication has been shown to be severely retarded in monocytes and macrophages (Balliet et al, 1994; and Westervelt et al, 1992).

Nevertheless, Vpu has been labelled as an "accessory" protein of HIV because none of its known functions appear to be essential for virus replication in vitro.

To improve the prospect of treating and preventing HIV infection, there is an on-going need to identify molecules capable of inhibiting various aspects of the HIV life cycle. In work leading up to the present invention, the inventors have surprisingly determined that despite current dogma, viral replication (and in particular HIV replication) can be retarded by inhibiting or otherwise down-regulating Vpu ion channel functioning. Further, the inventors have also determined that although the drug amiloride has no effect on HIV replication, amiloride analogues, in which the $H_2N$ group located at the 5-position of the pyrazine has been substituted, inhibit Vpu function and thereby inhibit the continuation of the HIV life cycle.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains nucleotide and amino acid sequence information prepared using the programme PatentIn Version 2.0, presented herein after the bibliography. Each nucleotide or amino acid sequence is identified in the sequence listing by the numeric indicator <210> followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212> and <213>, respectively. Nucleotide and amino sequences referred to in the specification are defined by the information provided in numeric indictor field <400> followed by the sequence identifier (e.g. <400>1, <400>2, etc).

One aspect of the present invention provides a method of reducing, retarding or otherwise inhibiting the functional activity of a virus, which virus has infected a mammalian host cell, said method comprising administering to said mammal an effective amount of an agent for a time and under conditions sufficient to down-regulate a membrane ion channel functional activity of said host cell.

Another aspect of the present invention more particularly provides a method of reducing, retarding or otherwise inhibiting the functional activity of HIV, which HIV has infected a mammalian host cell, said method comprising administering to said mammal an effective amount of an agent for a time and under conditions sufficient to down-regulate the Vpu ion channel functional activity of said host cell.

Still another aspect of the present invention provides a method of reducing, retarding or othewise inhibiting HIV replication, which HIV has infected a mammalian host cell, said method comprising administering to said mammal an effective amount of an agent for a time and under conditions sufficient to down-regulate the Vpu ion channel functional activity of said host cell.

Yet another aspect of the present invention provides a method of reducing, retarding or otherwise inhibiting the functional activity of HIV, which HIV has infected a mammalian macrophage, said method comprising administering to said mammal an effective amount of an agent for a time and under conditions sufficient to down-regulate the Vpu ion channel functional activity of said macrophage.

Still yet another aspect of the present invention provides a method of reducing, retarding or otherwise inhibiting HIV replication, which HIV has infected a mammalian host cell, said method comprising contacting said host cell with an effective amount of an amiloride analogue, or functional equivalent thereof, for a time and under conditions sufficient to inhibit Vpu ion channel functional activity.

A further aspect of the present invention provides a method of reducing, retarding or otherwise inhibiting HIV replication, which HIV has infected a mammalian host cell, said method comprising contacting said host cell with an effective amount of HMA or functional equivalent thereof for a time and under conditions sufficient to inhibit Vpu ion channel mediation of HIV replication.

Another further aspect of the present invention provides a method of reducing, retarding or otherwise inhibiting HIV replication which HIV has infected a mammalian host cell, said method comprising contacting said host cell with an effective amount of DMA or functional equivalent thereof for a time and under conditions sufficient to inhibit Vpu ion channel mediation of HIV replication.

Still another further aspect provides a method for the treatment and/or prophylaxis of HIV infection or AIDS in a mammal said method comprising administering to said mammal an effective amount of an agent for a time and under conditions sufficient to down-regulate the Vpu ion channel functional activity of an HIV infected mammalian host cell, wherein said Vpu functional activity down-regulation reduces, retards or otherwise inhibits the functional activity of said HIV.

Still yet another further aspect provides a method for the treatment and/or prophylaxis of HIV infection or AIDS in a mammal said method comprising administering to said mammal an effective amount of an agent for a time and under conditions sufficient to down-regulate the Vpu ion channel functional activity of an HIV infected mammalian host cell, wherein said Vpu functional activity down-regulation reduces, retards or otherwise inhibits HIV replication. Another aspect of the present invention provides a method of reducing, retarding or otherwise inhibiting membrane ion channel functional activity in a subject said method comprising administering to said subject an effective amount of an amiloride analogue or functional equivalent thereof for a time and under conditions sufficient to inhibit membrane ion channel functional activity.

Yet another aspect of the present invention provides a method of reducing, retarding or otherwise inhibiting Vpu ion channel functional activity in a mammal said method comprising administering to said mammal an effective amount of an amiloride analogue or functional equivalent thereof for a time and under conditions sufficient to inhibit Vpu ion channel functional activity.

Still another aspect of the present invention provides a method of reducing, retarding or otherwise inhibiting Vpu ion channel mediation of HIV replication in a mammal said method comprising administering to said mammal an effective amount of an amiloride analogue or functional equivalent thereof for a time and under conditions sufficient to inhibit Vpu ion channel functional activity.

Still yet another aspect of the present invention provides an agent useful for reducing, retarding or otherwise inhibiting Vpu ion channel functional activity as hereinbefore defined.

Still another aspect of the present invention provides a composition for use in reducing, retarding or otherwise inhibiting Vpu ion channel functional activity comprising an agent as hereinbefore defined and one or more pharmaceutically acceptable carriers and/or diluents.

DETAILED DESCRIPTION OF THE PREFERRED EMBODIMENTS

Figure 1B:
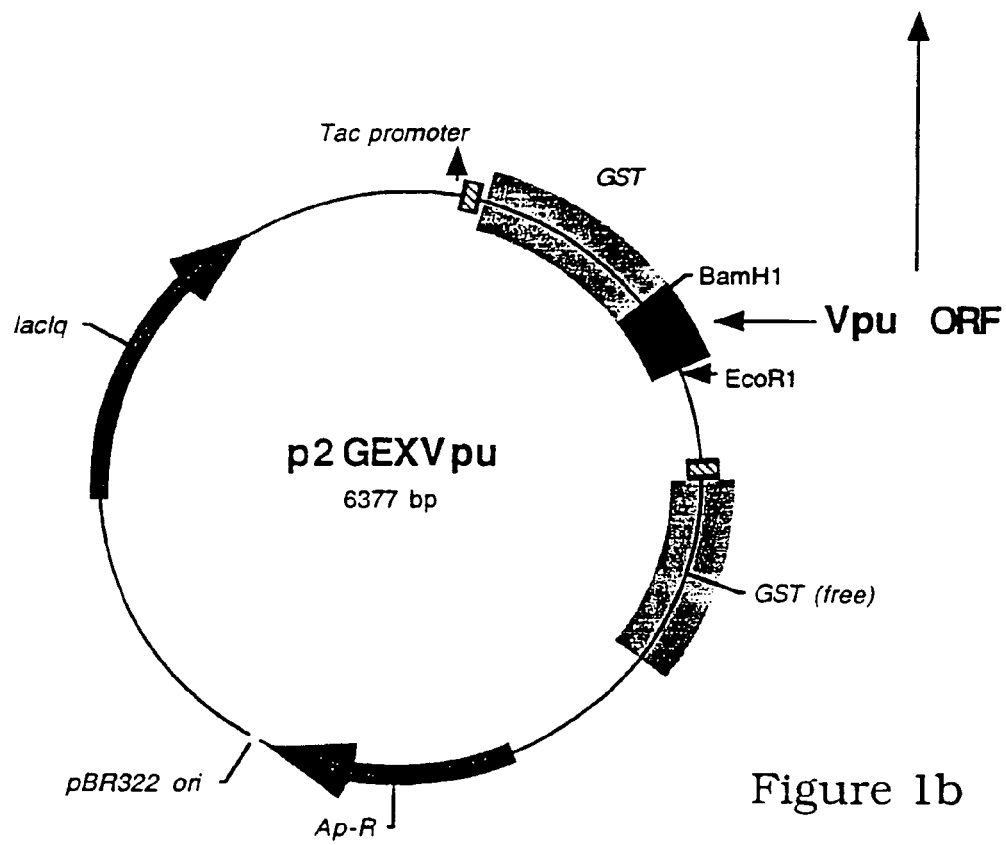
FIG. 1 is a schematic representation of plasmids used for expression of Vpu in *E. coli* A. The amino acid sequence (<400>1) encoded by the vpu open reading frame (ORF) generated by PCR from an HIV-1 strain HXB2 cDNA clone. The vpu ORF was cloned in-frame at the 3' end of the GST gene in p2GEX to generate p2GEXVpu (B). It was subsequently cloned into pPL451 to produce the plasmid pPL+Vpu (C).

The present invention is predicated, in part, on the surprising determination that the replication of viruses which cause a host cell to express a Vpu ion channel, in particular HIV, can be retarded by inhibiting the functioning of this ion channel. Further, although amiloride has no effect on HIV replication, amiloride analogues are able to inhibit the HIV life cycle by inhibiting Vpu ion channel functioning. This determination now permits the use of agents such as, but not limited to, amiloride analogues as anti-viral agents for the therapy and prophylaxis of viral conditions.

Accordingly, one aspect of the present invention provides a method of reducing, retarding or otherwise inhibiting the functional activity of a virus, which virus has infected a mammalian host cell, said method comprising administering to said mammal an effective amount of an agent for a time and under conditions sufficient to down-regulate a membrane ion channel functional activity of said host cell.

Reference to "membrane ion channel" should be understood as a reference to a structure which transports ions across a membrane. The present invention extends to ion channels which may function by means such as passive, osmotic, active or exchange transport. The ion channel may be formed by intracellular or extracellular means. For example, the ion channel may be an ion channel which is naturally formed by a cell to facilitate its normal functioning. Alternatively, the ion channel may be formed by extracellular means. Extracellular means would include, for example, the formation of ion channels due to introduced chemicals, drugs or other agents such as ionophores or due to the functional activity of viral proteins encoded by a virus which has entered a cell. Preferably, the ion channel of the present invention is an ion channel which results from the infection of a cell with HIV and, more particularly, the ion channel is formed by the HIV protein Vpu (referred to herein as a "Vpu ion channel").

The ion channels which are the subject of the present invention facilitate the transport of ions across membranes. Said membrane may be any membrane and is not limited to the outer cell wall plasma membrane. Accordingly, "membrane" encompasses the membrane surrounding any cellular organelle, such as the Golgi apparatus and endoplasmic reticulum, the outer cell membrane, the membrane surrounding any foreign antigen which is located within the cell (for example, a viral envelope) or the membrane of a foreign organism which is located extracellularly. The membrane is typically, but not necessarily, composed of a fluid lipid bilayer. The subject ion channel may be of any structure. For example, the Vpu ion channel is formed by Vpu which is an integral membrane protein encoded by HIV-1 which associates with, for example, the Golgi and endoplasmic reticulum membranes of infected cells. Reference hereinafter to "Vpu ion channels" 110 should be read as including reference to all other ion channels.

Accordingly, the present invention more particularly provides a method of reducing, retarding or otherwise inhibiting the functional activity of HIV, which HIV has infected a mammalian host cell, said method comprising administering to said mammal an effective amount of an agent for a time and under conditions sufficient to down-regulate the Vpu ion channel functional activity of said host cell.

Reference to "HIV" should be understood as a reference to any HIV strain and including homologues and mutants.

Without limiting the present invention in any way, Vpu is a protein comprising approximately 80 amino acids with an N-terminal transmembrane anchor and a hydrophilic cytoplasmic C-terminal domain. The C-terminal domain typically comprises a 12 amino acid sequence that is conserved and contains two serine residues which are phosphorylated (Schubert et al, 1994 and Friborg et al, 1995). Vpu is an integral membrane protein encoded by HIV-1. It associates with the Golgi and endoplasmic reticulum membranes in infected cells, but has not been detected in the viral envelope nor in the plasma membrane of cells except when artificially over-expressed (Schubert et al, 1996a). without limiting the present invention in any way, Vpu has the capacity to form homo-oligomers, but the exact number of subunits in the native complex is not known. The secondary structure and tertiary fold of the cytoplasmic domain of Vpu has been determined by a combination of NMR and CD spectroscopy and molecular dynamics calculations (Willbold et al, 1997) and reveals two α-helices separated by a short flexible loop containing the phosphorylated serine residues. Recent structural data for the transmembrane domain (Wray et al, 1999) supports the theoretical prediction that the region is α-helical and indicates a tilt angle of less than 30° to the bilayer normal. Two molecular dynamics simulation studies have been reported based on the assumption that oligomerisation produces a bundle of α-helixes that spans the membrane (Grice et al, 1997; and Moore et al, 1998). Both studies favour formation of a pentameric complex. However, using different initial conditions and restraint parameters, different conclusions as to the orientation of the individual helices in the complex were reached. Thus, the actual structure of the native Vpu complex remains to be determined.

In spite of the fact that Vpu has been shown by the inventors to form ion channels, prior to the advent of the present invention it was not known that ion channel formation by Vpu was a function which is critical to the life cycle of the HIV virus.

Reference to the "functional activity" of an ion channel should be understood as a reference to any one or more of the functions which an ion channel performs or is involved in. For example, the Vpu protein encoded ion channel, in addition to facilitating the transportation of $Na^+$, $K^+$, $Cl^-$ and $PO_4^{3-}$, also plays a role in the degradation of the CD4 molecule in the endoplasmic reticulum. The Vpu protein encoded ion channel is also thought to play a role in mediating the HIV life cycle since inactivating this channel inhibits the HIV life cycle, in particular, the replication of HIV. However, the present invention is not limited to treating HIV infection via the mechanism of inhibiting the HIV life cycle and, in particular, HIV replication. Rather, the present invention should be understood to encompass any mechanism by which inhibiting Vpu ion channel functional activity acts to reduce, retard or otherwise inhibit HIV viability or functional activity. Said functional activity is preferably mediation of the replication of HIV. In this regard, reference to the "functional activity" of a virus should be understood as a reference to any one or more of the functions which a virus performs or is involved in. This includes, for example, viral replication and budding. Preferably, said functional activity is HIV replication.

Reference to the "HIV replication" should be understood to include any one or more stages or aspects of the HIV life cycle, such as inhibiting the assembly or release of HIV virons. Said Vpu mediation of HIV replication may be by direct or indirect means. Said Vpu mediation is by direct means if the Vpu ion channel interacts directly with HIV at any one or more of its life cycle stages. Said Vpu mediation is indirect if it acts on a molecule other than HIV which other molecule either directly or indirectly modulates any one or more aspects or stages of the HIV life cycle. Accordingly, the method of the present invention encompassess the mediation of HIV replication via the induction of a cascade of steps which lead to the mediation of any one or more aspects or stages of the HIV life cycle.

According to this preferred embodiment, the present invention provides a method of reducing, retarding or othewise inhibiting HIV replication, which HIV has infected a mammalian host cell, said method comprising administering to said mammal an effective amount of an agent for a time and under conditions sufficient to down-regulate the Vpu ion channel functional activity of said host cell.

Reference to "down-regulating" ion channel functional activity, and in particular Vpu mediation of HIV replication should be understood as a reference to the partial or complete inhibition of any one or more aspects of said activity by both direct and indirect mechanisms. For example, a suitable agent may interact directly with a Vpu ion channel to prevent HIV replication or, alternatively, may act indirectly to prevent said replication by, for example, interacting with a molecule other than the Vpu ion channel wherein said other molecule interacts with and inhibits the activity of the Vpu ion channel.

The inhibition of ion channel functional activity may be achieved by any suitable method, which would be well known to those skilled in the art, including contacting a virally infected cell with a proteinaceous or non-proteinaceous molecule capable of blocking or otherwise down-regulating functioning of the subject ion channel. Screening for molecules which block Vpu ion channel activity may be achieved for by any suitable method including, for example, the method disclosed in Example 11. It should also be understood that the down-regulation of ion channel functional activity may be achieved by transfecting a cell, such as the subject host cell, with a nucleic acid molecule which expresses a molecule capable of blocking or otherwise down-regulating functioning of the subject ion channel. Accordingly, reference to "agent" should be understood as a reference to any proteinaceous or non-proteinaceous molecule, including nucleic acid molecules, which directly or indirectly inhibit Vpu ion channel functional activity. Reference to an "agent" should be understood to include reference to functional equivalents and derivatives thereof of said agent.

Reference to a "mammalian host cell" infected with HIV should be understood as a reference to any cell which has been infected with HIV. This includes, for example, an infected CD4$^+$ cell or an infected monocyte or macrophage. Without limiting the present invention in any way, the ability of HIV-1 to infect and efficiently replicate in macrophages is thought to be essential in AIDS pathogenesis. In fact, it has been suggested that macrophage-tropic HIV isolates may be necessary and sufficient for the development of AIDS. Accordingly, in a preferred embodiment the subject HIV infected cell is a HIV infected macrophage or monocyte.

According to this preferred embodiment there is provided a method of reducing, retarding or otherwise inhibiting the functional activity of HIV, which HIV has infected a mammalian macrophage, said method comprising administering to said mammal an effective amount of an agent for a time and under conditions sufficient to down-regulate the Vpu ion channel functional activity of said macrophage.

In another preferred embodiment there is provided a method of reducing, retarding or otherwise inhibiting the functional activity of HIV, which HIV has infected a mammalian macrophage, said method comprising administering to said mammal an effective amount of an agent for a time and under conditions sufficient to down-regulate the Vpu ion channel functional activity of said monocyte.

In a related aspect, the inventors have also surprisingly determined that analogues of amiloride inhibit Vpu ion channel functional activity. This was an unexpected result due to the prima facie incompatible structure of the subject analogue with the Vpu ion channel. Specifically, without limiting the present invention to any one theory or mode of action, amiloride analogues are thought to inhibit HIV viron release from cells by causing the Vpu ion channels to become blocked. This blocking is effected by substituted amiloride but not by unsubstituted amiloride. Unsubstituted amiloride is a pyrazinoylguanidine bearing amino groups on the 3- and 5-positions and a chloro group on the 6-position of the pyrazine ring. However, the present invention should not be understood as limited to analogues of this form of amiloride or functional equivalents thereof. The present invention encompasses analogues of any form of amiloride. For example, other isomeric forms of amiloride. Accordingly, reference to "amiloride analogue" should be understood as a reference to any amiloride molecule which exhibits an addition, deletion or substitution, such as an addition, deletion or substitution of an atom or molecule or changing of the charge of an atom or molecule, at any position but more particularly at any one or more of the 6 positions of the pyrazine ring. Preferably, said amiloride analogue is an amiloride molecule exhibiting a substitution of the amino group at the 5-position of the pyrazine ring.

Accordingly, in a preferred embodiment the present invention provides a method of reducing, retarding or otherwise inhibiting HIV replication, which HIV has infected a mammalian host cell, said method comprising contacting said host cell with an effective amount of an amiloride analogue, or functional equivalent thereof, for a time and under conditions sufficient to inhibit Vpu ion channel functional activity.

Preferably, said amiloride analogue comprises a substitution of the amino group at the 5-position of the pyrazine ring or functional equivalent thereof. Even more preferably, said Vpu ion channel functional activity is Vpu ion channel mediation of HIV replication.

Still more preferably, said amiloride analogue is 5-(N,N-Hexamethylene)-Amiloride (referred to herein as "HMA") or 5-(N,N-Dimethyl)-Amiloride (referred to herein as "DMA").

According to this preferred embodiment there is provided a method of reducing, retarding or otherwise inhibiting HIV replication, which HIV has infected a mammalian host cell, said method comprising contacting said host cell with an effective amount of HMA or functional equivalent thereof for a time and under conditions sufficient to inhibit Vpu ion channel mediation of HIV replication.

In another preferred embodiment there is provided a method of reducing, retarding or otherwise inhibiting HIV replication which HIV has infected a mammalian host cell, said method comprising contacting said host cell with an effective amount of DMA or functional equivalent thereof for a time and under conditions sufficient to inhibit Vpu ion channel mediation of HIV replication.

Most preferably said amiloride analogues comprise the structure:

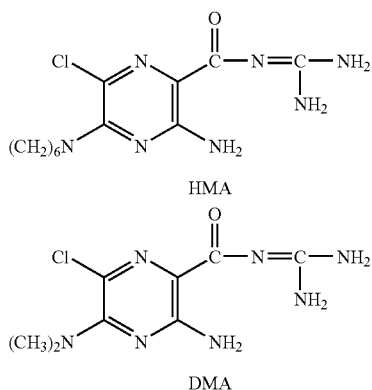

HMA

DMA

"Functional equivalents" of amiloride analogues and any other proteinaceous or non-proteinacous agents which exhibit functional activity equivalent to the amiloride analogues (to the extent that Vpu ion channel functional activity is inhibited or otherwise down-regulated as hereinbefore defined), include functionally active derivatives, fragments, parts, portions and chemical equivalents from natural, synthetic or recombinant sources, including fusion proteins. Chemical equivalents may not necessarily be derived from the subject agent but may share certain conformational similarity. Alternatively, chemical equivalents may be specifically designed to mimic certain physiochemical properties of the agent. Chemical equivalents may be chemically synthesised or may be detected following, for example, natural product screening. Functional equivalents may also possess antagonistic or agonistic properties and the use of such molecules are contemplated by the present invention.

Where the agent or functional equivalent is a proteinaceous molecule, the present invention should be understood to extend to functional derivatives of said proteinaceous molecule. Derivatives include fragments, parts, portions, mutants, and mimetics from natural, synthetic or recombinant sources including fusion proteins. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutanmine; serine and threonine; lysine and arginine; and phenylalanine and tyrosine. Additions to amino acid sequences including fusions with other peptides, polypeptides or proteins.

Homologs of the protein contemplated herein include, but are not limited to, proteins derived from different species.

The derivatives include fragments having particular epitopes of parts of the entire protein fused to peptides, polypeptides or other proteinaceous or non-proteinaceous molecules. For example, a protein (or a non-proteinaceous molecule) or derivative thereof may be fused to a molecule to facilitate its entry into a cell.

Reference to "derivatives" should also be understood to include reference to analogues. Analogues contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |

TABLE 1-continued

| Non-conventional amino acid | Code | Non-conventional amino acid | Code |
|---|---|---|---|
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

The subject of the viral inhibition is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably, the subject is a human or primate. Most preferably, the subject is a human.

The method of the present invention is useful in the treatment and prophylaxis of HIV infection and AIDS. For example, the down-regulation of Vpu ion channel functional activity may be effected in subjects known to be infected with HIV in order to prevent replication of HIV thereby preventing the onset of AIDS. Alternatively, the method of the present invention may be used to reduce serum viral load or to alleviate AIDS symptoms.

The method of the present invention may be particularly useful either early in HIV infection to prevent the establishment of a viral reservoir in cell types such as monocytes and macrophages or as a prophylactic treatment to be applied immediately prior to or for a period after exposure to a possible source of HIV infection.

Accordingly, in another aspect there is provided a method for the treatment and/or prophylaxis of HIV infection or AIDS in a mammal said method comprising administering to said mammal an effective amount of an agent for a time and under conditions sufficient to down-regulate the Vpu ion channel functional activity of an HIV infected mammalian host cell, wherein said Vpu functional activity down-regulation reduces, retards or otherwise inhibits the functional activity of said HIV.

More particularly, the present invention provides a method for the treatment and/or prophylaxis of HIV infection or AIDS in a mammal said method comprising administering to said mammal an effective amount of an agent for a time and under conditions sufficient to down-regulate the Vpu ion channel functional activity of an HIV infected mammalian host cell, wherein said Vpu functional activity down-regulation reduces, retards or otherwise inhibits HIV replication.

Reference to "an effective amount" means an amount necessary to at least partly attain the desired response.

Reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of onset of a particular condition. "Treatment" may also reduce the severity of an existing condition or the frequency of acute attacks.

Preferably said agent is an amiloride analogue or functional equivalent thereof. Even more preferably, said amiloride analogue is HMA or DMA.

In accordance with this method, more than one type of agent may be administered or the agent may be co-administered with another molecule such as a known anti-viral compound or molecule. By "co-administered" is meant simultaneous administration in the same formulation or in two different formulations via the same or different routes or sequential administration by the same or different routes. By "sequential" administration is meant a time difference of from seconds, minutes, hours or days between the administration of the two types of an amiloride analogue or the amiloride analogue and the known anti-viral compound or molecule. The subject agent and known anti-viral compound or molecule may be administered in any order.

Routes of administration include but are not limited to intravenously, intraperitionealy, subcutaneously, intracranialy, intradermally, intramuscularly, intraocularly, intrathecaly, intracerebrally, intranasally, by infusion, orally, rectally, via iv drip, patch and implant. Intravenous routes are particularly preferred.

The present invention further extends to the use of the subject agents in the manufacture of a medicament for the therapeutic or prophylactic treatment of HIV infection or AIDS in a mammal wherein said agent reduces, retards or otherwise inhibits Vpu ion channel functional activity of an HIV infected cell.

Preferably said functional activity is mediation of HIV replication.

Most preferably said agent is an amiloride analogue or functional equivalent thereof and still more preferably HMA or DMA or functional equivalent thereof.

As detailed previously, the inventors have surprisingly determined that although amiloride has no effect on Vpu ion channel functional activity, amiloride analogues are able to block functional activity.

Accordingly, another aspect of the present invention provides a method of reducing, retarding or otherwise inhibiting membrane ion channel functional activity in a subject said method comprising administering to said subject an effective amount of an amiloride analogue or functional equivalent thereof for a time and under conditions sufficient to inhibit membrane ion channel functional activity.

More particularly, the present invention provides a method of reducing, retarding or otherwise inhibiting Vpu ion channel functional activity in a mammal said method comprising administering to said mammal an effective amount of an amiloride analogue or functional equivalent thereof for a time and under conditions sufficient to inhibit Vpu ion channel functional activity.

Still more preferably, the present invention provides a method of reducing, retarding or otherwise inhibiting Vpu ion channel mediation of HIV replication in a mammal said method comprising administering to said mammal an effective amount of an amiloride analogue or functional equivalent thereof for a time and under conditions sufficient to inhibit Vpu ion channel functional activity.

Preferably, said amiloride analogue comprises a substitution of the amino group of the 5-position of the pyrazine ring or functional equivalent thereof.

Even more preferably, said amiloride analogue is HMA or DMA.

Most preferably, said amiloride analogues comprise the structure:

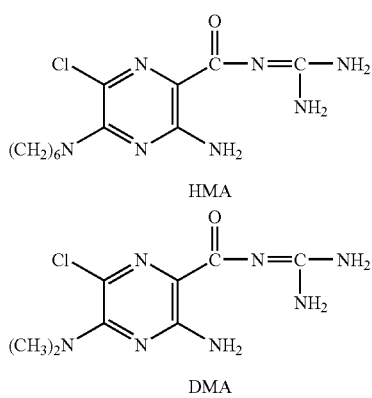

Yet another aspect of the present invention provides an agent useful for reducing, retarding or otherwise inhibiting Vpu ion channel functional activity as hereinbefore defined.

Preferably said functional activity is mediation of HIV replication.

Most preferably said agent is an amiloride analogue or functional equivalent thereof and even more particularly said agent is HMA or DMA or functional equivalent thereof.

Still another aspect of the present invention provides a composition for use in reducing, retarding or otherwise inhibiting Vpu ion channel functional activity comprising an agent as hereinbefore defined and one or more pharmaceutically acceptable carriers and/or diluents. The composition may also comprise two different types of agents or an agent and a known anti-viral compound or molecule.

Preferably said inhibition of ion channel functional activity is inhibition of Vpu ion channel mediation of HIV replication.

Compositions suitable for injectable use include sterile aqueous solutions (where water soluble) and sterile powders for the extemporaneous preparation of sterile injectable solutions. They must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ng and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels. In such forms, the anti-clotting peptides may need to be modified to permit penetration of the surface barrier.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding.

Effective amounts contemplated by the present invention will vary depending on the severity of the pain and the health and age of the recipient. In general terms, effective amounts may vary from 0.01 ng/kg body weight to about 100 mg/kg body weight. Alternative amounts include for about 0.1 ng/kg body weight about 100 mg/kg body weight or from 1.0 ng/kg body weight to about 80 mg/kg body weight.

Further features of the present invention are more fully described in the following Examples. It is to be understood, however, that the detailed description is included solely for the purpose of exemplifying the present invention. It should not be understood in any way as a restriction on the broad description of the invention as set out above.

EXAMPLE 1

Construction of Recombinant Plasmids p2GEXVpu and pPLVpu

The open reading frame encoding Vpu (FIG. 1a) was amplified by PCR from a cDNA clone of an Nde 1 fragment of the HIV-1 genome (isolate HXB2, McFarlane Burnet Centre, Melbourne, Australia). Native Pfu DNA polymerase (Stratagene; 0.035 U/μl) was chosen to catalyse the PCR reaction to minimise possible PCR introduced errors by virtue of the enzyme's proofreading activity. The 5', sense, primer AGTA<u>GGATCC</u>ATGCAACCTATACC (<400>2) introduces a BamH1 site (underlined) for cloning in-frame with the 3' end of the GST gene in p2GEX (41). This primer also repairs the start codon (bold T replaces a C) of the vpu gene which is a threonine codon in the HXB2 isolate. The 3', antisense, primer TCTG<u>GAATTC</u>TACAGATCAT CAAC (<400>3) introduces an EcoR1 site (underlined) to the other end of the PCR product to facilitate cloning. After 30 cycles of 94° C. for 45 sec, 55° C. for 1 min and 72° C. for 1 min in 0.5 ml thin-walled eppendorf tubes in a Perkin-Elmer thermocycler, the 268 bp fragment was purified, digested with BamH1 and EcoR1 and ligated to p2GEX prepared by digestion with the same two enzymes. The resultant recombinant plasmid is illustrated in FIG. 1b. The entireVpu open reading frame and the BamH1 and EcoR1 ligation sites were sequenced by cycle sequencing, using the Applied Biosystems dye-terminator kit, to confirm the DNA sequence.

Figure 1C:
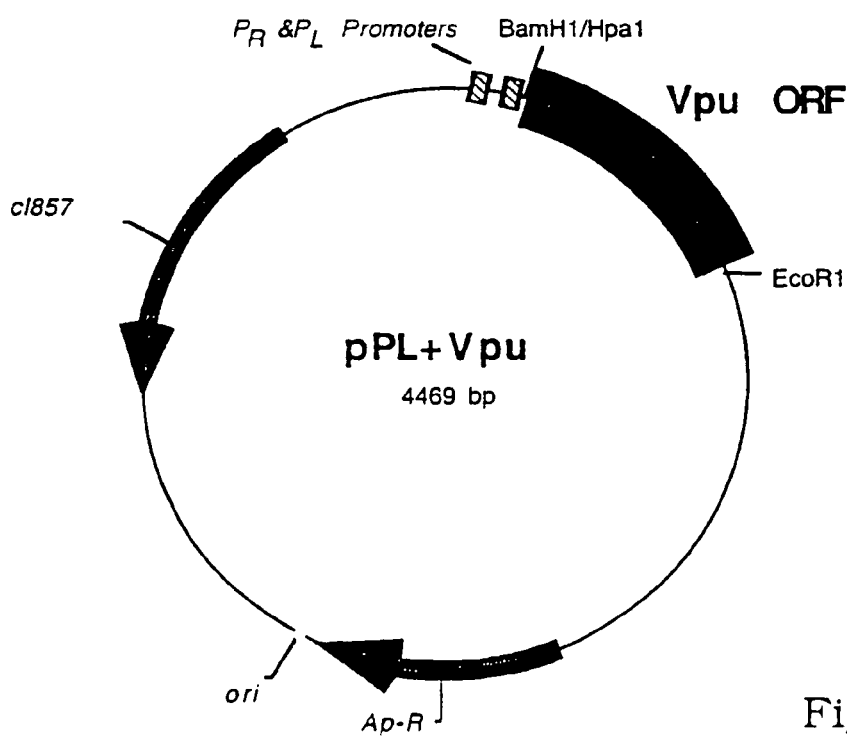

To prepare the Vpu open reading frame for insertion into the pPL451 expression plasmid, p2GEXVpu was first digested with BamH1 and the 5' base overhang was filled in the Klenow DNA polymerase in the presence of dNTPs. The Vpu-encoding fragment was then liberated by digestion with EcoR1, purified from an agarose gel and ligated into pPL451 which had been digested with Hpa1 and EcoR1. Western blots subsequently confirmed that the pPLVpu construct (FIG. 1c) expressed Vpu after induction of cultures at 42° C. to inactivate the c1857 repressor of the PR and PL promoters.

EXAMPLE 2

Raising Polyclonal Antibodies for Immuno-Identification of VPU

A peptide CALVEMGVEMGHHAPWDVDDL (<400>4) corresponding to the C-terminal 20 amino acid residues of Vpu was synthesised in the Biomolecular Resource Facility (ANU, Australia) using an Applied Biosystems model 477A machine. A multiple antigenic peptide (MAP) was prepared (Lu et al, 1991) by coupling the peptide to a polylysine core via the N-terminal cysteine residue. The MAP was used to immunise rabbits for production of polyclonal antisera recognising the C-terminus of Vpu. For immunisations 1 mg of MAP peptide was dissolved in 1.25 ml of MTPBS (16 mM $Na_2HPO_4$, 4 mM $NaHPO_4$, 150 mM NaCl pH 7.3) and emulsified with 1.25 ml of Freund's complete adjuvant and injected at multiple subcutaneous sites on the rabbit's back. Booster injections used Freund's incomplete adjuvant and were spaced at least 4 weeks apart with serum being sampled 10–14 days after injections.

EXAMPLE 3

Techniques Involving the Antibodies

Peptide-specific antibodies were purified from rabbit sera using an Immunopure™ Ag/Ab Immobilisation kit from Pierce. The synthetic peptide was cross-linked via its N-terminal cysteine to the matrix of a 5 ml Sulfo Link™ column according to the kit's instructions, 2.5 ml of Vpu immunoreactive serum was added to 20 ml of Tris buffer (10 mM pH 7.4) and passed through the peptide column three times to maximise exposure of the antibodies to the peptide. The column was washed with 20 ml of 10 mM Tris pH 7.4 followed by 20 ml of the same buffer supplemented with 500 mM NaCl. The bound antibodies were eluted in 5 ml of 100 mM glycine/150 mM NaCl, pH 2.5 and eluents were immediately neutralised by addition of 250 μl of 1M Tris pH 9.0 and dialysed overnight against MTPBS.

An anti-Vpu immunoaffinity column was constructed by covalently cross-linking 200 μg of purified antibody to 100 μl of protein A agarose beads (Schleicher and Schuell) using the bifunctional cross-linking reagent dimethylpimelimidate as described previously (Harlow and Lane, 1988).

Immunoprecipitation of Vpu was performed by incubation of samples in the presence of approximately 5-fold excess of purified antibody (room temperature for 1 hr)

followed by addition of excess protein-A agarose, incubation for 30 min, and centrifugation to pellet the Vpu-antibody complexes. The supernatant, which was subsequently used as a control in the electrophysiological bilayer experiments, was tested by western blotting to confirm that Vpu had been completely removed. Protein samples were electrophoresed on homogeneous 18% SDS polyacrylamide gels using a minigel apparatus and prepoured gels (Novex). Samples were treated with SDS (3.2% final) and mercaptoethanol (0.8% final) at 60° C. for 5 min before loading onto gels. Protein bands were visualised either with Coomassie brilliant blue R250 or by silver staining.

For western blotting, proteins were transferred from acrylamide gels to PVDF membranes using a semi-dry transfer apparatus (Pharmacia LKB). Vpu was detected after consecutive reactions of the blots with polyclonal antiserum or purified antibodies, goat anti-rabbit alkaline phosphatase conjugate and Western Blue™ stabilised substrate (Promega).

EXAMPLE 4

Purification of Recombinant Vpu from E. Coli

Cultures of *E. coli* strain XL1-blue cells containing p2GEXVpu were grown at 30° C. with vigorous aeration in LB medium supplemented with glucose (6 g/L) and ampicillin (50 mg/L) to a density of approximately 250 Klett units, at which time IPTG was added to a final concentration of 0.01 mM and growth was continued for a further 4 hr. The final culture density was approximately 280 Klett units. Since early experiments revealed that the majority of expressed GST-Vpu fusion protein was associated with both the cell debris and membrane fractions, the method of Varadhachary and Maloney (Varadhachary and Maloney, 1990) was adopted to isolate osmotically disrupted cell ghosts (combining both cell debris and membrane fractions) for the initial purification steps. Cells were harvested, washed, weighed and resuspended to 10 ml/g wet weight in MTPBS containing DTT (1 mM) and $MgCl_2$ (10 mM). Lysozyme (0.3 mg/ml; chicken egg white; Sigma) was added and incubated on ice for 30 min with gentle agitation followed by 5 min at 37° C. The osmotically sensitised cells were pelleted at 12,000 g and resuspended to the original volume in water to burst the cells. The suspension was then made up to 1×MTPBS/DTT using a 10× buffer stock and the ghosts were isolated by centrifugation and resuspended in MTPBS/DTT to which was then sequentially added glycerol (to 20% wt/vol) and CHAPS (to 2% wt/vol) to give a final volume of one quarter the original volume. This mixture was stirred on ice for 1 hr and then centrifuged at 400,000 g for 1 hr to remove insoluble material. The GST-Vpu fusion protein was purified from the detergent extract by affinity chromatography on a glutathione agarose resin (Sigma). The resin was thoroughly washed in 50 mM Tris pH 7.5 containing glycerol (5%), DTT (1 mM), and CHAPS (0.5%) (Buffer A) and then the Vpu portion of the fusion protein was liberated and eluted from the resin-bound GST by treatment of a 50% (v/v) suspension of the beads with human thrombin (100 U/ml; 37° C. for 1 hr). PMSF (0.5 mM) was added to the eluant to eliminate any remaining thrombin activity. This Vpu fraction was further purified on a column of MA7Q anion exchange resin attached to a BioRad HPLC and eluted with a linear NaCl gradient (0–2M) in buffer A.

The Vpu was purified to homogeneity—as determined on silver stained gels—on an immunoaffinity column as follows: HPLC fractions containing Vpu were desalted on a NAP column (Pharmacia) into buffer A and then mixed with the antibody-agarose beads for 1 hr at room temperature. The beads were washed thoroughly and Vpu was eluted by increasing the salt concentration to 2M. Protein was quantitated using the BioRad dye-binding assay.

EXAMPLE 5

Reconstitution of Vpu in Phospholipid Vesicles

Proteoliposomes containing Vpu were prepared by the detergent dilution method (New, 1990). A mixture of lipids (PE:PC:PS; 5:3:2; 1 mg total lipid) dissolved in chloroform was dried under a stream of nitrogen gas and resuspended in 0.1 ml of potassium phosphate buffer (50 mM pH 7.4) containing DTT (1 mM). A 25 µl aliquot containing purified Vpu was added, followed by octylglucoside to a final concentration of 1.25% (wt/vol). This mixture was subject to three rounds of freezing in liquid nitrogen, thawing and sonication in a bath-type sonicator (20–30 sec) and was then rapidly diluted into 200 volumes of the potassium phosphate buffer. Proteoliposomes were collected by centrifugation at 400,000 g for 1 hr and resuspended in approximately 150 µl of phosphate buffer.

EXAMPLE 6

Assaying Ion Channel Activity

Purified Vpu was tested for its ability to induce channel activity in planar lipid bilayers using standard techniques as described elsewhere (Miller, 1986; and Piller et al, 1996). The solutions in the CIS and TRANS chambers were separated by a Delrin™ plastic wall containing a small circular hole of approximately 100 µm diameter across which a lipid bilayer was painted so as to form a high resistance electrical seal. Bilayers were painted from a mixture (8:2) of palmitoyl-oleoly-phosphatidyl-ethanolamine and palmitoyl-oleoly-phosphatidyl-choline (Avanti Polar Lipids, Alabaster, Ala.) in n-decane. The solutions in the two chambers contained MES buffer (10 mM, pH 6.0) to which various NaCl or KCl concentrations were added. Currents were recorded with an Axopatch™ 200 amplifier. The electrical potential between the two chambers could be manipulated between ±200 mV (TRANS relative to grounded CIS). Aliquots containing Vpu were added to the CIS chamber either as a detergent solution or after incorporation of the protein into phospholipid vesicles. The chamber was stirred until currents were observed.

EXAMPLE 7

Testing the Effect of HMA and DMA on HIV Replication in Human Monocytes and Macrophages Human monocytes were isolated from peripheral blood and cultured either for 24 hr (one day old monocytes) or for 7 days to allow differentiation into monocyte derived macrophages (MDM). These cells were then exposed to cell-free preparations of HIV isolates and allowed to absorb for 2 hr before complete aspiration of the medium, washing once with virus-free medium and resuspension in fresh medium. The cells were exposed to 50–10 µM HMA or DMA either 24 hr prior to infection or after infection. Subsequent HIV replication, at various times after infection, was compared in cells exposed to drugs and in cells not exposed to drugs (controls). The progression and extent of viral replication was assayed using either an HIV DNA PCR method (Fear et al, 1998) or an ELISA method to quantitate p24 in culture supernatants (Kelly et al, 1998).

EXAMPLE 8

Expression and Purification of Vpu in E. Coli

The plasmid p2GEXVpu (FIG. 1) was constructed to create an in-frame gene fusion between the GST and Vpu open-reading frames. This system enabled IPTG-inducible expression of the Vpu polypeptide fused to the C-terminus of GST and allowed purification of the fusion protein by affinity chromatography on glutathione agarose.

Figure 2A:
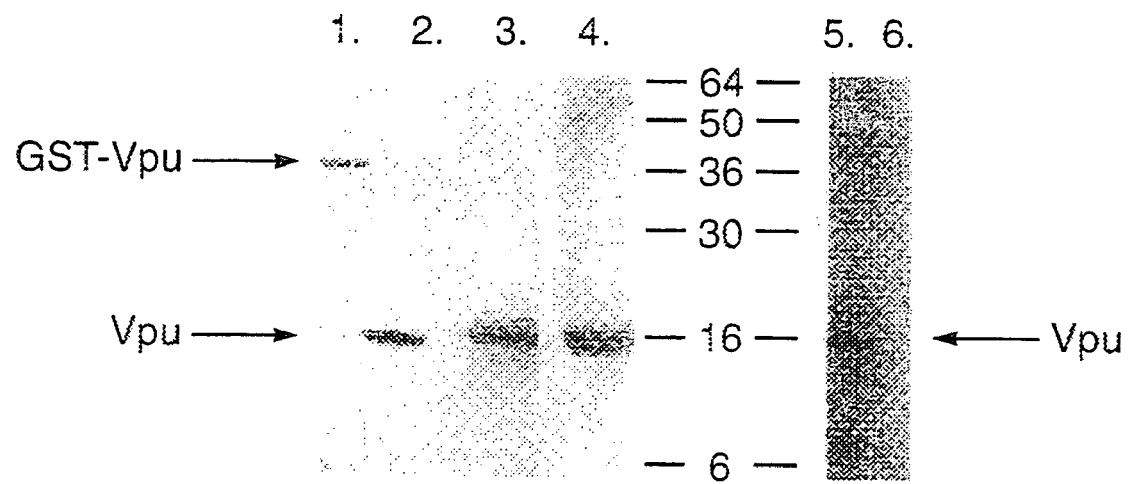
FIG. 2 is a photographic representation of the expression and purification of Vpu in *E. coli*. A. Western blotting after SDS-PAGE was used to detect expressed Vpu in *E. coli* extracts. Lanes 1–4 contain samples, at various stages of purity, of Vpu expressed from p2GEXVpu: lane 1, GST-Vpu fusion protein isolated by glutathione-agarose affinity chromatography; lane 2, Vpu liberated from the fusion protein by treatment with thrombin; lane 3, Vpu purified by HPLC anion exchange chromatography; lane 4, Vpu after passage through the immunoaffinity column. Lanes 5 and 6, membrane vesicles prepared from 42° C. induced cells containing pPL+Vpu or pPL451, respectively. B. Silver stained SDS-PAGE gel: lane 1, Vpu purified by HPLC anion exchange chromatography; lane 2, Vpu after passage through the immunoaffinity column.
Figure 2B:
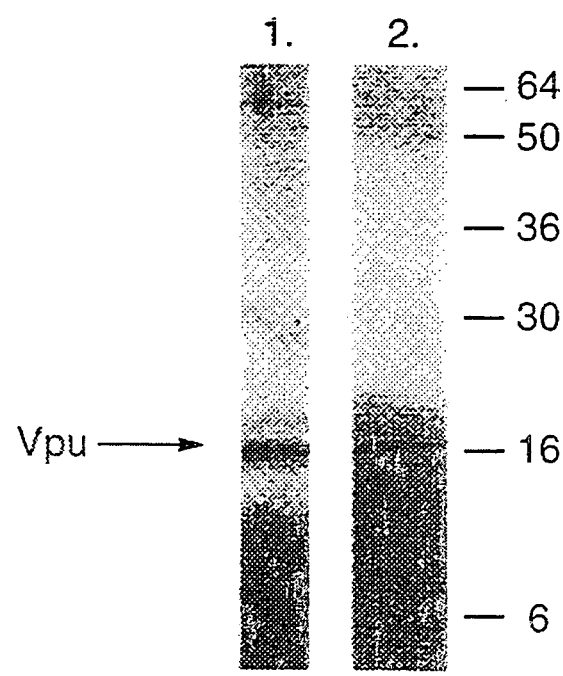

Optimal levels of GST-Vpu expression were obtained by growing the cultures at 30° C. to a cell density of approximately 250–300 Klett units and inducing with low levels of IPTG (0.01 mM). To purify the GST-Vpu, a combined cellular fraction containing the cell debris and plasma membrane was prepared by lysozyme treatment of the induced cells followed by a low-speed centrifugation. Approximately 50% of the GST-Vpu protein could be solubilised from this fraction using the zwitterionic detergent CHAPS. Affinity chromatography using glutathione-agarose beads was used to enrich the fusion protein and thrombin was used to cleave the fusion protein at the high affinity thrombin site between the fusion partners, liberating Vpu (FIG. 2A). In fractions eluted from the anion exchange column Vpu was the major protein visible on silver stained gels (FIG. 2B, lane 1). Finally, Vpu was purified to apparent homogeneity on an immunoaffinity column (FIG. 2B, lane 2). The N-terminal amino acid sequence of the protein band (excised from SDS-PAGE gels) corresponding to the immunodetected protein confirmed its identity as Vpu.

EXAMPLE 9

Vpu Forms Ion Channels in Lipid Bilayers

Figure 3A:
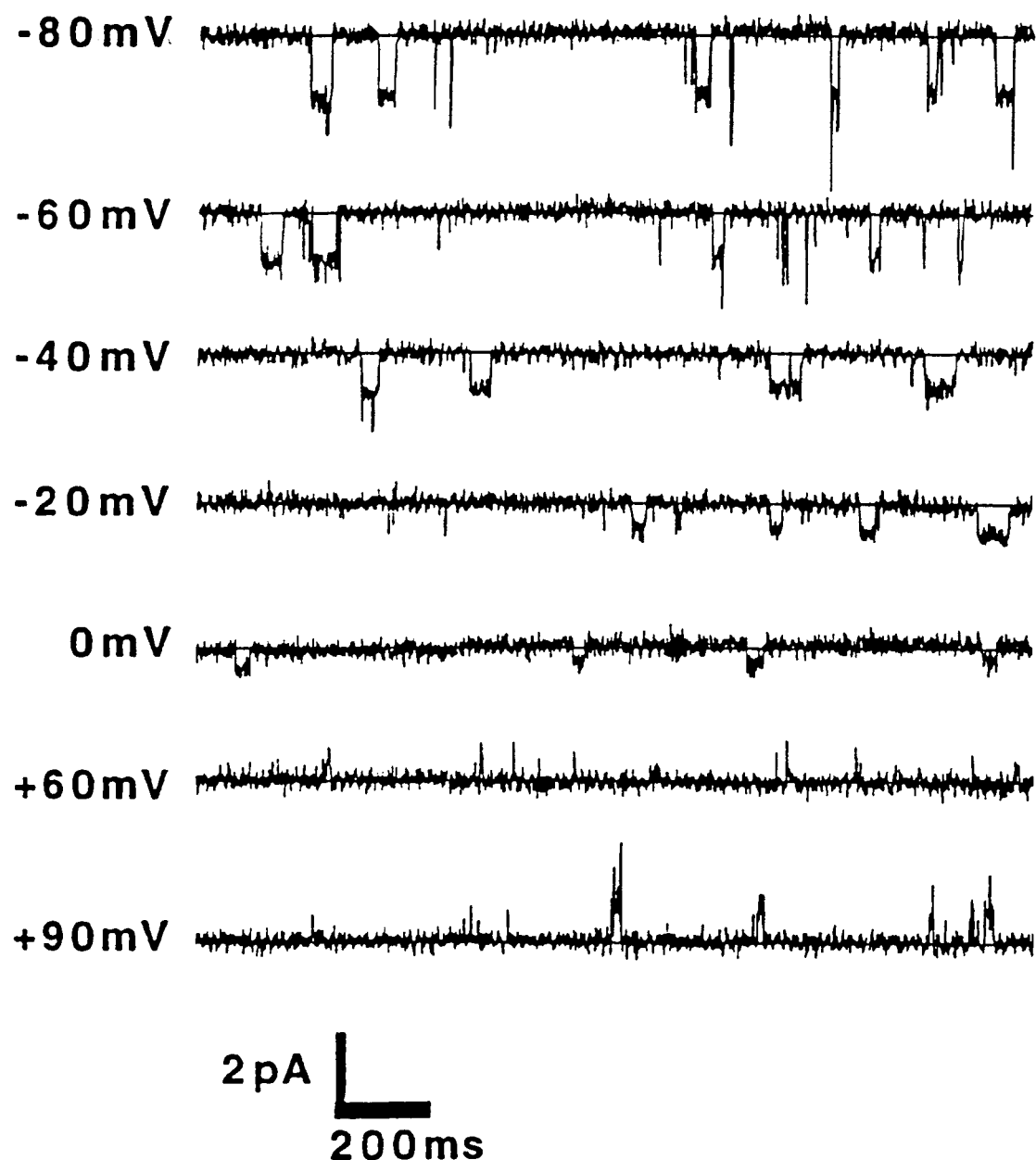
FIG. 3 is a graphical representation of ion channel activity observed after exposure of lipid bilayers to aliquots containing purified Vpu. In A and B, the CIS chamber contained 500 mM NaCl and the TRANS chamber contained 50 mM NaCl; both solutions were buffered at pH 6.0 with 10 mM MES. B shows a current versus voltage curve generated from data similar to that shown in A.

To assay for ion-channel formation by Vpu, reconstitution into planar lipid bilayers was performed. When samples (containing between 7 and 70 ng of protein) of purified recombinant Vpu were added to the 1 ml of buffer in the CIS chamber of the bilayer apparatus, current fluctuations were detected after periods of stirring that varied from 2 to min (FIG. 3). This time taken to observe channel activity approximately correlated with the amount of protein added to the chamber. No channels were detected when control buffer aliquots or control lipid vesicles were added to the CIS chamber. In those control experiments the chambers could be stirred for more than an hour without appearance of channel activity.

EXAMPLE 10

Properties of the Vpu Channels

Channel activity was observed in over 40 individual experiments with Vpu samples prepared from five independent purifications. In different experiments, the amplitude of the currents varied over a large range and, again, seemed to approximately correlate with the amount of protein added. The smallest and largest channels measured had conductances of 14 pS and 280 pS, respectively. The channels were consistently smaller when lipid vesicles containing Vpu were prepared and fused to the bilayer rather than when purified protein in detergent solution was added. This may be because the former method included treatment with high concentrations of detergent and a dilution step that may have favoured the breakdown of large aggregates into monomers.

Figure 3B:
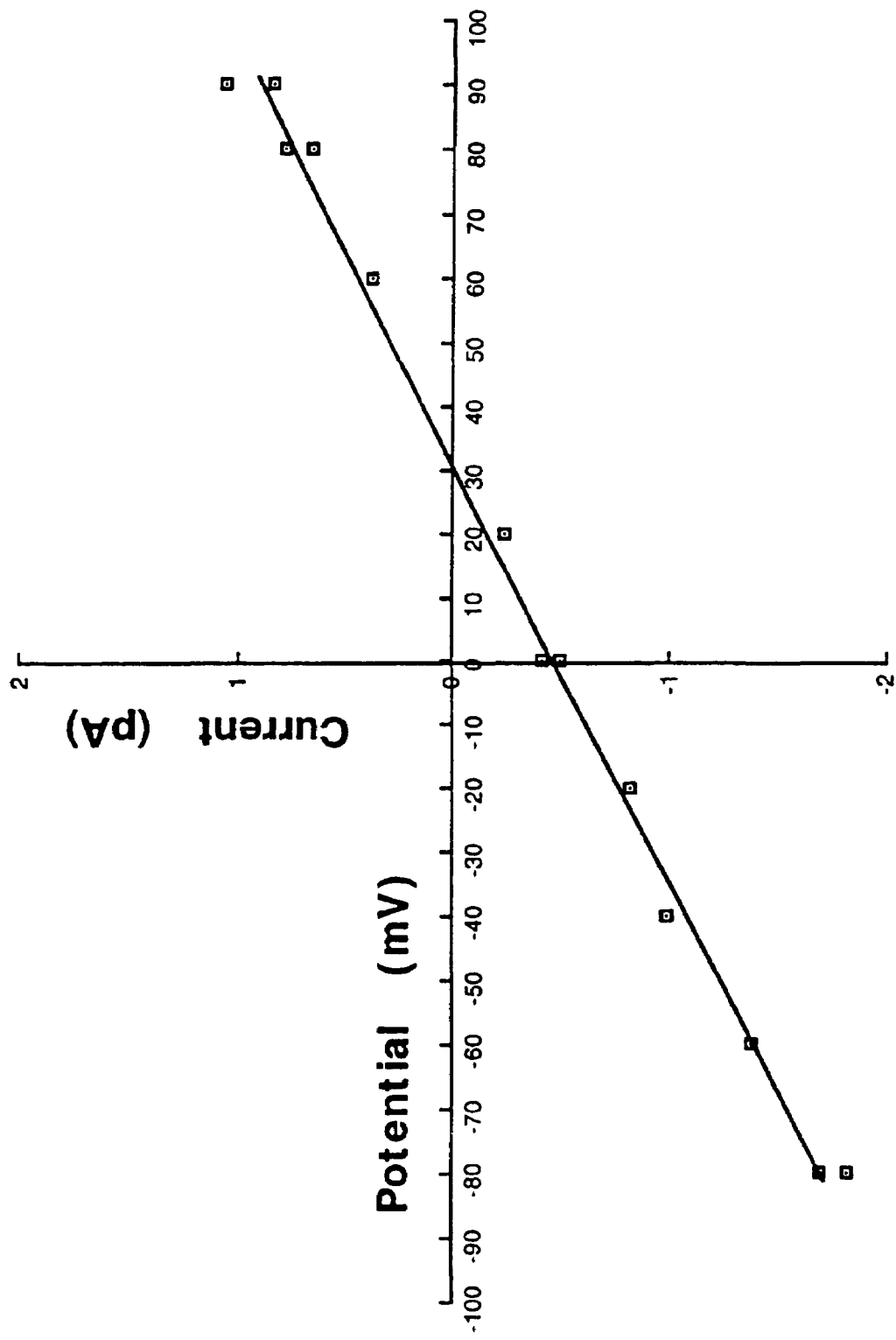

The relationship between current amplitude and voltage was linear and the reversal potential in solutions containing a ten-fold gradient of NaCl (500 mM CIS; 50 mM TRANS) was +30 mV (FIG. 3B). A similar reversal potential was obtained when solutions contained KCl instead of NaCl. In 5 experiments with either NaCl or KCl in the solutions on either side of the membrane, the average reversal potential was 31.0±1.2 mV (±SEM). This is more negative than expected for a channel selectively permeable for the cations alone. Using ion activities in the Goldman-Hodgkin-Katz equation gives a $P_{Na}/P_{cl}$ ratio of about 5.5 indicating that the channels are also permeable to chloride ions. An attempt was made to reduce the anion current by substituting phosphate for chloride ions. When a Na-phosphate gradient (150 mM $Na^+$ & 100 mM phosphate CIS; 15 mM $Na^+$ & 10 mM phosphate TRANS, pH 6.8) was used instead of the Na Cl gradient, the reversal potential was 37.1±0.2 (±SEM, n=2) again indicating a cation/anion permeability ratio of about 5. (For calculations involving the phosphate solutions, the summed activities of the mono and bivalent anions were used and it was assumed that the two species were equally permeable). The current-voltage curve now exhibited rectification that was not seen in the NaCl solutions. It can be concluded that the channels formed by Vpu are equally permeably to $Na^+$ and $K^+$ and are also permeable, though to a lesser extent, to chloride as well as phosphate ions.

EXAMPLE 11

Bio-Assay for Screening Potential Ion-Channel Blocking Drugs

As part of a search for drugs that block the Vpu ion channel, a novel bio-assay was developed to facilitate the screening process which would be prohibitively slow if performed in the bilayer assay (Ewart et al, 1996). This bio-assay is based on the observation that expression of Vpu in E. coli results in an active Vpu channel located in the plasmalemma that dissipates the transmembrane sodium gradient. As a consequence of this Vpu channel activity, metabolites whose accumulation within the cells is mediated by a sodium dependent co-transporter (for example proline or adenine) leak out of the cell faster than they can be synthesised so that the metabolites' intracellular levels become limiting for growth of the cell. Thereby, an E. coli cell expressing Vpu is unable to grow in minimal drop-out media lacking adenine or proline. However, in the presence of a drug that blocks the Vpu channel, the cell is once again able to re-establish its transmembrane sodium gradient— due to the action of other ion pumps in the membrane—and the leakage of metabolites is prevented enabling growth. Experiments to demonstrate that Vpu can form sodium channels in the plasma membrane of E. coli were performed as follows:

To express unfused Vpu in E. coli, the vpu open-reading frame was cloned into the plasmid pPL451 (19) to create the recombinant plasmid pPL-Vpu (FIG. 1b). In this vector the strong $P_L$ and $P_R$ lambda promoters are used to drive expression of Vpu under control of the temperature sensitive cI857 represser, such that when grown at 30° C. expression is tightly repressed and can be induced by raising the temperature to between 37° C. and 42° C. On agar plates, cells containing pPL-Vpu grew when incubated at 30° C. and 37° C. but not at 42° C., while control strains grew well at 42°

C. Liquid cultures of cells containing pPL-Vpu were grown at 30° C. to $OD_{600}$=0.84 then moved to grow at 42° C. for two hours (the final cell density was $OD_{600}$=0.75). The plasma membrane fraction was prepared and western blotting, using an antibody that specifically binds to the C-terminus of Vpu, detected a single band at approximately 16 kDa, indicating that Vpu was expressed and associated with the membranes (FIG. 2A, lane 5).

EXAMPLE 12

Cross-Feeding Experiments Reveal that Proline Leaks Out of Cells Expressing Vpu

Figure 4A:
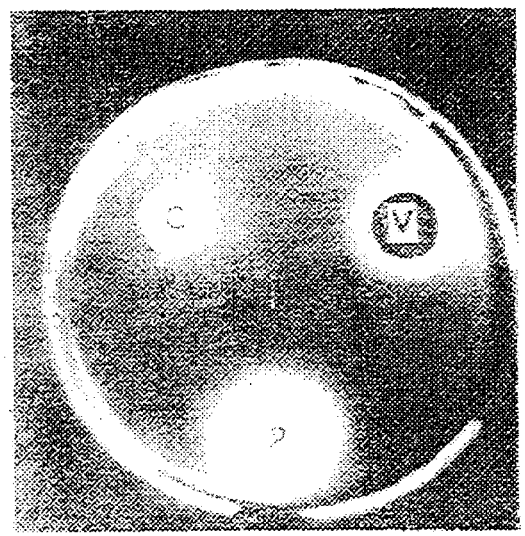
FIG. 4 is a photographic representation of bacterial cross-feeding assays. For all plates, the Met$^-$, Pro$^-$ auxotrophic strain was used to seed a soft agar overlay. Plates A and B contain minimal drop-out medium minus proline; in plate C the medium was minus methionine. To control for viability of the cells in the background lawn, the discs labelled P and M contained added proline or methionine, respectively. The discs labelled C and V were inoculated with Met$^+$, Pro$^+$ *E. coli* cells containing the plasmids pPL451 or pPL+Vpu, respectively. Plates were incubated at 37° C. (A and C) or 30° C. (B) for two days and photographed above a black background with peripheral illumination from a fluorescent light located below the plate. The images were recorded on a Novaline video gel documentation system. Light halos around the discs labelled P or M on all plates and around the disc labelled V on plate A indicate growth of the background lawn strain.
Figure 4B:
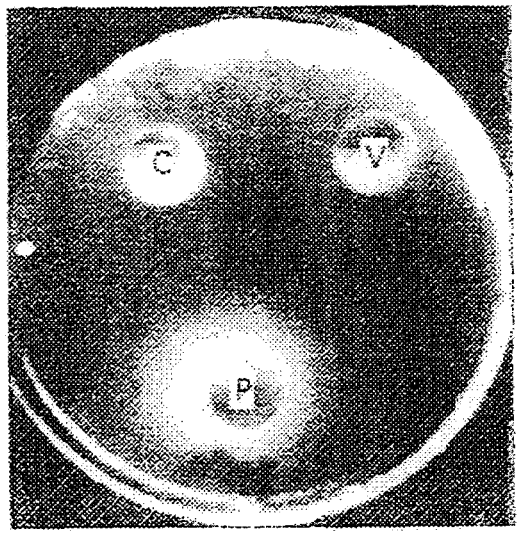

Uptake of proline by *E. coli* is well characterised and active transport of the amino acid into the cells is known to use the sodium gradient as the energy source (Yamato et al, 1994). To detect whether proline leakage occurs, the following cross-feeing assay was used: A lawn of an *E. coli* strain auxotrophic for proline and methionine (Met$^-$Pro$^-$), was seeded and poured as a soft agar overlay on minimal drop-out media plates lacking proline but containing methionine. Sterile porous filter discs were inoculated with a Met$^+$Pro$^-$ strain (XL-1 blue) containing either the pPL451 control plasmid or pPL-Vpu and placed onto the soft agar. The plates were then incubated at 37° C. or 30° C. for two days. After than time a halo growth of the Met$^-$ Pro$^-$ strain was clearly visible surrounding the disc inoculated with the cells containing pPL-Vpu incubated at 37° C. (FIG. 4A). This growth can only be due to the leakage of proline from the Vpu-expressing cells on the disc. No such leakage was apparent from the control strain at 37° C. nor around either strain on plates grown at 30° C. (FIG. 4B).

Figure 4C:
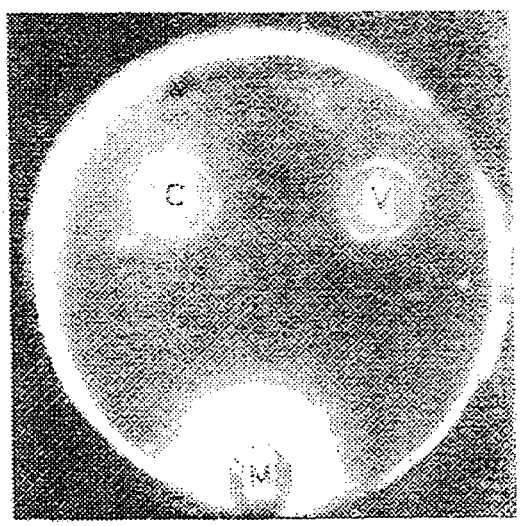

In contrast to proline transport, the *E. coli* methionine permease is known to belong to the ABC transporter family (Rosen, 1987) and hence be energised by ATP. Identical cross-feeding experiments to those described above were set us except that the Met$^-$ Pro$^-$ strain was spread on minimal drop-out plates lacking methionine but containing proline. No growth of this strain was evident around any of the discs (FIG. 4C), indicating that methionine was not leaking out of the XL-1 blue cells even when Vpu was being expressed.

EXAMPLE 13

E. Coli Cells Expressing Vpu Require Adenine in the External Medium for Growth

It was observed that, due to an uncharacterised mutation in the adenine synthesis pathway, growth of *E. coli* cells of the XL1-blue strain expressing Vpu at 37° C. was dependant on the presence of adenine in the medium. This allowed the development of an even simpler bio-assay for Vpu ion-channel activity than the proline cross-feeding assay described above: A lawn of XL1-blue cells containing the pPL-Vpu plasmid is seeded onto an agarose plate lacking adenine in the medium, small aliquots of drugs to be tested for inhibition of the Vpu channel are spotted onto the agarose in discrete locations and the plates are incubated at 37° C. for a suitable period of time (12–36 hours). Halos of growth around a particular drug application site indicate that the drug has inhibited expression of the Vpu ion channel activity that prevents growth in the absence of the drug.

EXAMPLE 14

Figure 5:
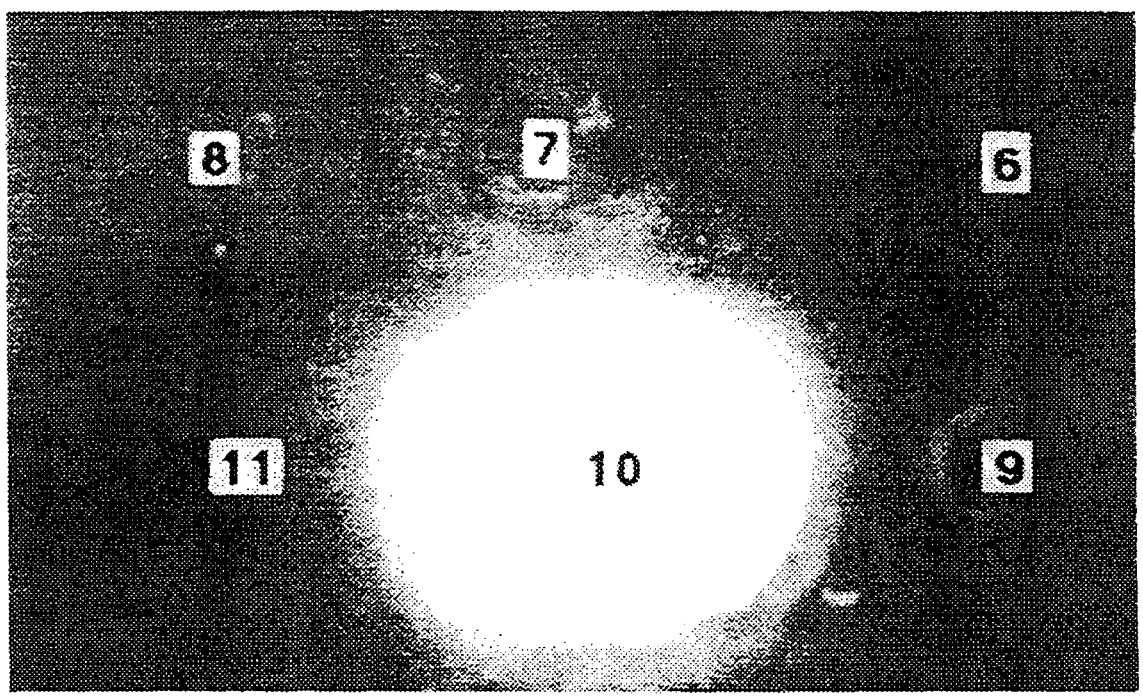
FIG. 5 is a graphical representation of the screening of drugs for potential Vpu channel blockers. The photograph shows a section of a minimal medium-lacking adenine-agarose plate onto which a lawn of XL-1-blue *E. coli* cells containing the Vpu expression plasmid pPLVpu has been seeded. Numbers 6–11 are located at the sites of application of various drugs being tested, which were applied in 3 μl drops and allowed to soak into the agarose. The plate was then incubated at 37° C. for 48 hr prior to being photographed. The background grey shade corresponds to areas of no bacterial growth. The bright circular area around "10" represents bacterial cell growth as a result of application of adenine at that location (positive control). The smaller halo of bacterial growth around "9" is due to the application of 5-(N,N-hexamethylene)-amiloride at that location.

The Bioassay Reveals 5-(N,N-Hexamethylene)-Amiloride as a Potential Channel Blocker Using this assay, a number of amantadine derivatives were tested but found not to affect channel activity. However, when a number of amiloride derivatives were also tested, a halo of growth around the site of application of 5-(N,N-Hexamethylene)-Amiloride (HMA) identified this drug as a potential Vpu channel blocker (FIG. 5). Unsubstituted amiloride did not produce a halo of bacterial growth on these plates.

EXAMPLE 15

Planar Lipid Bilayer Experiments Confirm HMA as a Vpu Channel Inhibitor

Figure 6:
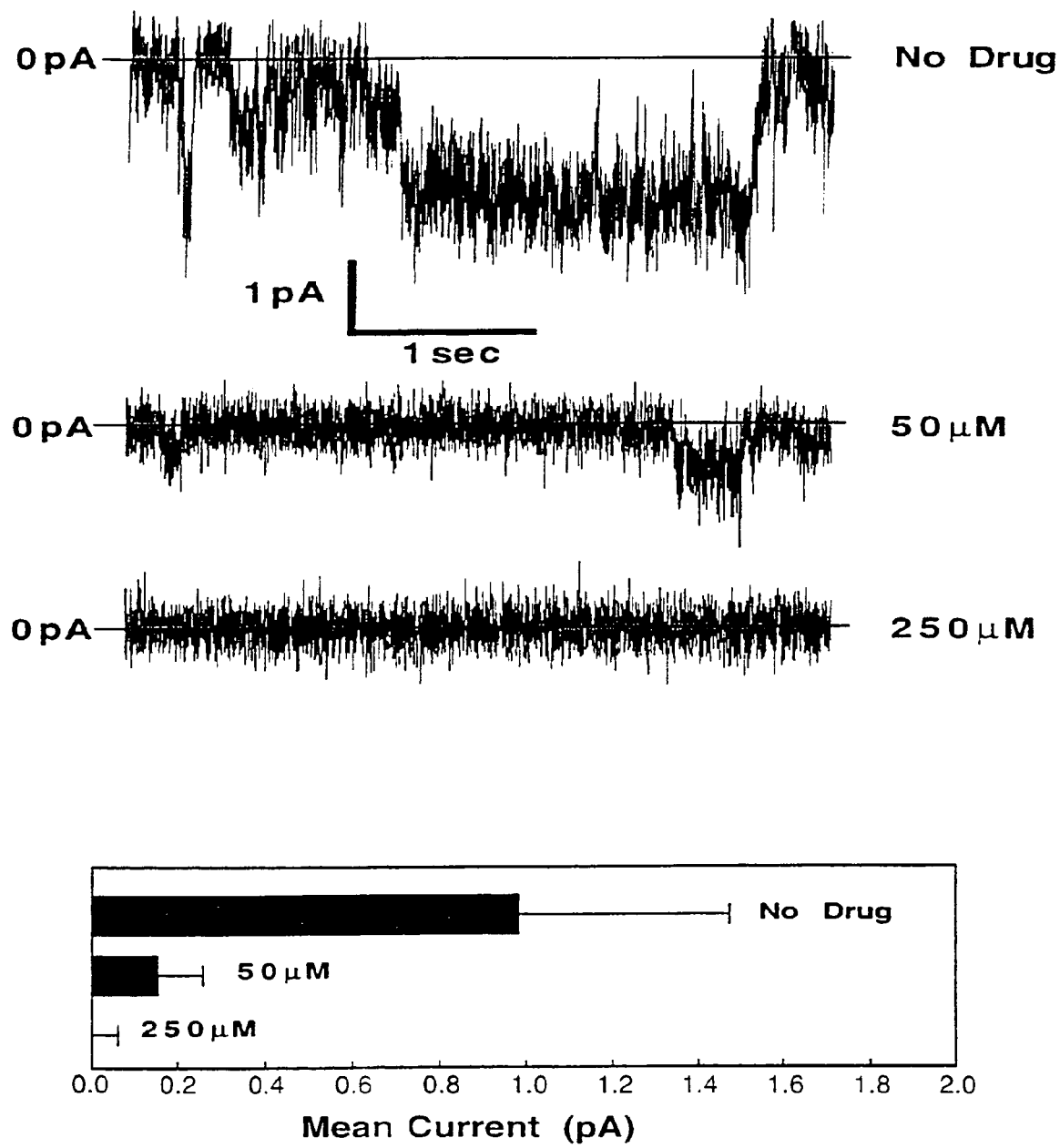
FIG. 6 is a graphical representation of the inhibition of Vpu ion channel activity by 5-(N,N-hexamethylene)-amiloride (HMA) in planar lipid bilayers. The three traces represent typical Vpu channel activity observed in the presence of the indicated concentrations of HMA. The solid line indicates the zero current level. Mean currents (± variance), calculated for continuous channel recordings of at least 30 seconds duration, are plotted in the graph for each of the three drug concentrations.

Inhibition of the Vpu ion-channel activity by HMA was confirmed in planar lipid bilayer experiments (FIG. 6), where concentrations of 50–250 μM HMA were found to block ion flow through the channel. The parent compound, amiloride, and another derivative, 5-(N,N-Dimethyl)-Amiloride (DMA), were similarly tested in planar lipid bilayer experiments: DMA was found to inhibit channel activity, though not as potently as HMA. Amiloride itself was not active as a channel blocker at these concentrations.

EXAMPLE 16

HMA AND DMA Inhibit HIV-1 Replication in Human Monocytes and Macrophages

Figure 7A:
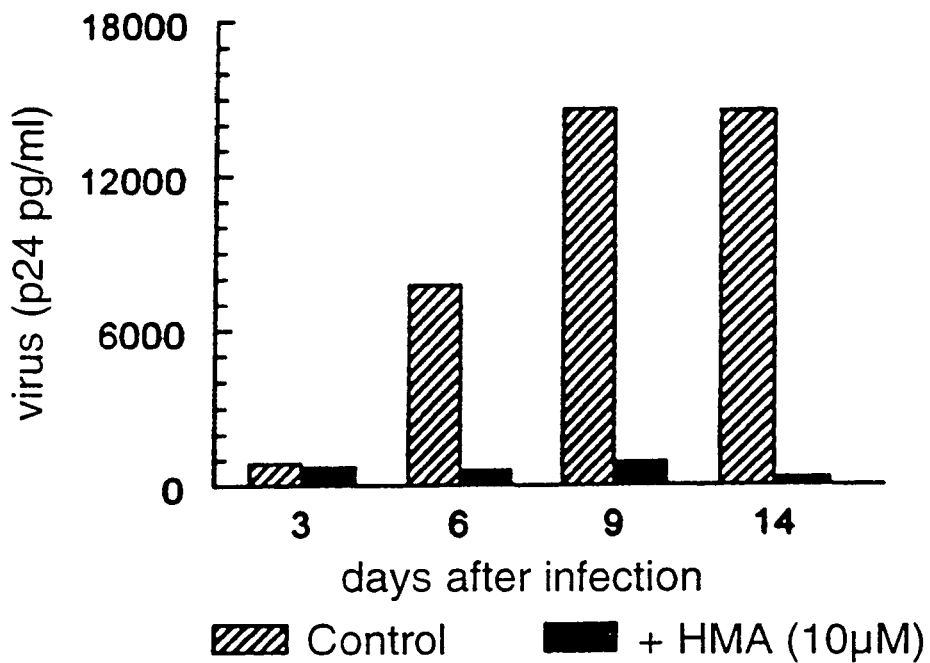
FIG. 7 is a graphical representation of the effect of HMA on HIV virion production in monocytes and monocyte-derived macrophages. HIV in culture supernatants was assayed at various days post-infection by detection of p24 antigen using a quantitative ELISA method. Solid black bars represent HIV-infected cells exposed to 10 μM HMA. Hatched bars are control cells not exposed to drug.
Figure 7B:
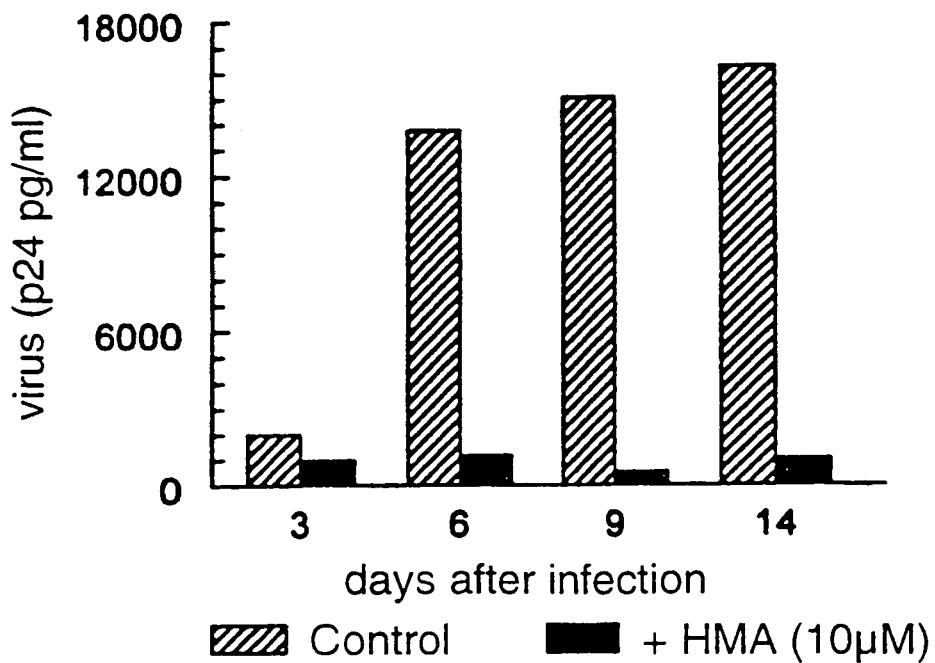
Figure 8:
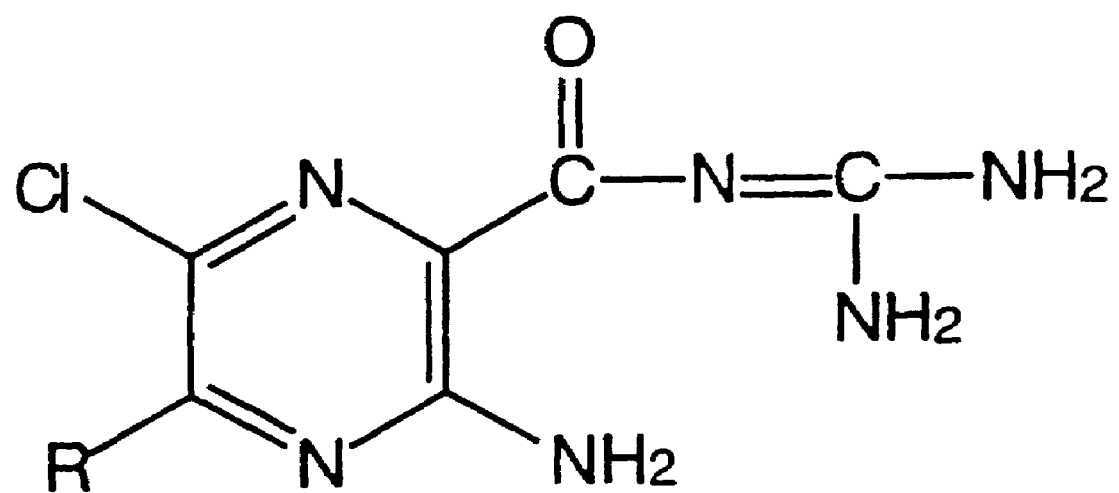
FIG. 8 is a schematic representation of the chemical formula of amiloride, HMA and DMA: R=H$_2$N, amiloride: R=(CH$_3$)$_2$N, DMA; R=(CH$_2$)$_6$N, HMA.

Subsequent tests were carried out to establish whether there was any anti-viral activity of HMA and DMA. Two tests were performed to characterise the effects of the drugs on HIV replication in human monocytes and macrophages: a) A PCR based assay was used to detect newly synthesised DNA arising from reverse transcription of the HIV genome, an early stage in virus replication; b) An ELISA method was used to quantitate production of the viral protein p24, reflecting a later stage in the replication process. Results of the PCR assay indicated that DMA at 50 μM inhibited synthesis of HIV DNA in the cells; HMA was toxic to the cells at 50 μM—further tests are being carried out at lower concentrations of this drug. p24 ELISA results indicated a clear inhibition of HIV virion synthesis with both DMA (50 μM, data not shown) and also with HMA (FIG. 7), when used at non-toxic levels (10 μM);

FIG. 7A shows the effect of HMA on monocytes, FIG. 7B shows the effect of HMA on macrophages.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Barry, M., Mulcahy, F. and Back, D. J., *Br J Clin Pharmacol*, 45: 221–8. (1998)

Deeks, S. G., *West J Med*, 168:133–9. (1998)

Miles, S. A., *J Acquir Immune Defic Syndr Hum Retrovirol*, 16 Suppl 1: S36–41. (1997)

Miles, S. A., *J. Acquir Immune Defic Syndr Hum Retrovirol*, 16 Suppl 1: S1–2. (1998)

Moyle, G. J., Gazzard, B. G., Cooper, D. A. and Gatell, J., *Drugs*, 55:383–404. (1998)

Rachlis, A. R. and Zarowny, D. P., *Cmaj*, 158:496–505. (1998)

Vella, S., Fragola, V. and Palmisano, L., *J Biol Regul Homeost Agents*, 11:60–3. (1997)

Volberding, P. A. and Deeks, S. G., *Jama*, 279:1343–4. (1998)

Volberding, P. A., *Hosp Pract (Off Ed)*, 33:81–4, 87–90, 95–6 passim. (1998)

Miller, R. H. and Sarver, N., *Nat Med*, 3:389–94. (1997)

Mitsuya, H., *Enzyme Inhibition*, 6:1–8. (1992)

Moore, J. P., *Science*, 276:51–2. (1997)

Thomas, M. and Brady, L., *Trends Biotechnol.*, 15:167–72. (1997)

Balliet, J. W., Kolson, D. L., Eiger, G., Kim, F. M., McGann, K. A., Srinivasan, A. and Collman, R., *Virology*, 200: 623–31. (1994)

Westervelt, P., Henkel, T., Trowbridge, D. B., Orenstein, J., Heuser, J., Gendelman, H. E. and Ratner, L., *J Virol*, 66:3925–31. (1992)

Ewart, G. D., Sutherland, T., Gage, P. W. and Cox, G. B., *J Virol*, 70:7108–7115. (1996)

Schubert, U., Henklein, P., Boldyreff, B., Wingender, E., Strebel, K. and Porstmann, T., *J Mol Biol*, 236:16–25. (1994)

Friborg, J., Ladha, A., Gottlinger, H., Haseltine, W. A. and Cohen, E. A., *Journal of Acquired Immune Deficiency Syndromes & Human Retrovirology*, 8:10–22. (1995)

Love, C. A., Lilley, P. E. and Dixon, N. E., *Escherichia coli. Gene*, in press. (1996)

Yamato, I., Kotani, M., Oka, Y. and Anraku, Y., *Escherichia coli. Journal of Biological Chemistry*, 269:5729–5724. (1994)

Rosen, B. R., ATP-coupled solute transport systems. *Escherichia coli* and *Salmonella typhimurium*: Cellular and molecular biology 1: (1987) Editor: Neidhardt, F. C. American Society for Microbiology.

Piller, S. C., Ewart, G. D., Premkumar, A., Cox, G. B. and Gage, P. W., *Proceedings of the National Academy of Sciences of the United States of America*, 93:111–115. (1996)

Lu, Y. A., Clavijo, P., Galantino, M., Shen, Z. Y., Liu, W. and Tam, J. P., *Molecular Immunology*, 28:623–630. (1991)

Harlow, E. and Lane, D., (1988) Antibodies: A laboratory manual. (ed). Cold Spring Harbor Laboratory, Cold Spring Harbor, N.Y., 'Vol:'.

Varadhachary, A. and Maloney, P. C., *Molecular Microbiology*, 4:1407–1411. (1990)

New, R. C. C., (1990). Liposomes: A practical approach. *The Practical Approach Series*. Rickwood, D., Hames, B. D. (eds). IRL Press, Oxford, pages, Miller, C., (1986) Ion channel reconstitution. (ed). Plenum Press, New York and London, 'Vol:'.

Fear, W. R., Kesson, A. M., Naif, H., Lynch, G. W. and Cunningham, A. L., *J. Virol*, 72:1334–1344. (1998)

Kelly, M. D., Naif, H., Adams, S. L., Cunningham, A. L. and Lloyd, A. R., *J. Immunol*, 160:3091–3095. (1998)

New, R. C. C. (ed.), Liposomes: a practical approach. IRL Press, Oxford (1990)

Grice, A. L., Kerr, I. D. and Sansom, M. S., *FEBS Lett*, 405(3):299–304 (1997)

Moore, P. B., Zhong, Q., Husslein, T. and Klein, M. L., *FEBS Lett*, 431(2):143–148 (1998)

Schubert, U., Bour, S., Ferrermontiel, A. V., Montal, M., Maldarelli, F. and Strebel, K., *Journal of Virology*, 70(2): 809–819 (1996a)

Willbold, D., Hoffmann, S. and Rosch, P., *Eur J Biochem*, 245(3):581–8 (1997)

Wray, V., Kinder, R., Federau, T., Henklein, P., Bechinger, B. and Schubert, U., *Biochemistry*, 38(16):5272–82 (1999)

---

The invention claimed is:

1. A method of reducing, retarding or otherwise inhibiting the functional activity of HIV, which HIV has infected a mammalian host cell, said method comprising administering to said mammal an effective amount of HMA or DMA for a time and under conditions sufficient to down-regulate a membrane ion channel functional activity of said host cell.

2. The method according to claim 1 wherein said membrane ion chanel is a Vpu ion channel.

3. The method according to claim 1 wherein said HIV functional activity is HIV replication.

4. The method according to claim 3 wherein said host cell is macrophage.

5. The method according to claim 3 wherein said host cell is a monocyte.

6. The method according to claim 1 wherein said HMA comprises the structure:

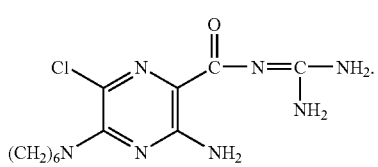

7. The method according to claim 1 wherein said DMA comprises the structure:

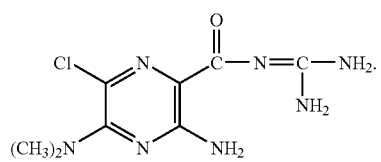

8. A method for the treatment and/or prophylaxis of HIV infection or AIDS in a mammal said method comprising administering to said mammal an effective amount of HMA or DMA for a time and under conditions sufficient to down-regulate the Vpu ion channel functional activity of an HIV infected mammalian host cell, wherein said Vpu functional activity reduces, retards or otherwise inhibits the functional activity of said HIV.

9. The method according to claim 8 wherein said HIV functional activity is HIV replication.

10. The method to claim 9 wherein said host cell is a macrophage.

11. The method according to claim 10 wherein said host cell is a monocyte.

12. The method according to claim 8 wherein said HMA comprise the structure:

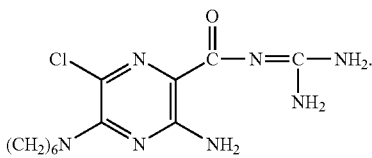

13. The method according to claim 8 wherein said DMA comprises the structure:

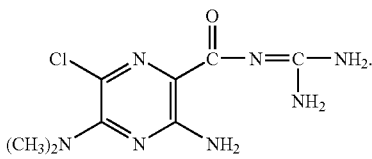

14. The method of reducing, retarding or otherwise inhibiting Vpu ion channel functional activity in a subject said method comprising administering to said subject an effective amount of HMA or DMA for a time and under conditions sufficient to inhibit Vpu ion channel functional activity.

15. The method according to claim 14 wherein said Vpu ion channel functional activity is Vpu ion channel mediation of HIV replication.

16. The method according to claim 14 wherein said HMA comprises the structure:

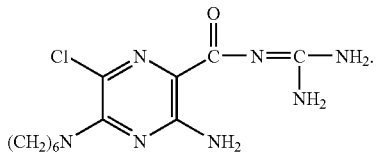

17. The method according to claim 14 wherein said DMA comprises the structure:

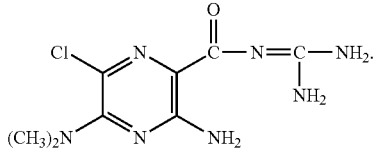

* * * * *

SEQUENCE LISTING

```
<160> NUMBER OF SEQ ID NOS: 4

<210> SEQ ID NO 1
<211> LENGTH: 82
<212> TYPE: PRT
<213> ORGANISM: HIV

<400> SEQUENCE: 1

Met Gln Pro Ile Pro Ile Val Ala Ile Val Ala Leu Val Val Ala Ile
 1               5                  10                  15

Ile Ile Ala Ile Val Val Trp Ser Ile Val Ile Ile Glu Tyr Arg Lys
            20                  25                  30

Ile Leu Arg Gln Arg Lys Ile Asp Arg Leu Ile Asp Arg Leu Ile Glu
        35                  40                  45

Arg Ala Glu Asp Ser Gly Asn Glu Ser Glu Gly Glu Ile Ser Ala Leu
    50                  55                  60

Val Glu Met Gly Val Glu Met Gly His His Ala Pro Trp Asp Val Asp
65                  70                  75                  80

Asp Leu
```

```
<210> SEQ ID NO 2
<211> LENGTH: 24
<212> TYPE: DNA
<213> ORGANISM: HIV

<400> SEQUENCE: 2
agtaggatcc atgcaaccta tacc                                              24

<210> SEQ ID NO 3
<211> LENGTH: 24
<212> TYPE: DNA
<213> ORGANISM: HIV

<400> SEQUENCE: 3
tctggaattc tacagatcat caac                                              24

<210> SEQ ID NO 4
<211> LENGTH: 21
<212> TYPE: PRT
<213> ORGANISM: HIV

<400> SEQUENCE: 4

Cys Ala Leu Val Glu Met Gly Val Glu Met Gly His His Ala Pro Trp
  1               5                  10                  15

Asp Val Asp Asp Leu
             20
```